United States Patent [19]

Goto et al.

[11] Patent Number: 4,816,180
[45] Date of Patent: Mar. 28, 1989

[54] NOVEL TOLAN TYPE LIQUID CRYSTAL COMPOUND

[75] Inventors: Yasuyuki Goto; Tetsuya Ogawa, both of Yokohamashi, Japan

[73] Assignee: Chisso Corporation, Osaka, Japan

[21] Appl. No.: 131,448

[22] Filed: Dec. 11, 1987

[30] Foreign Application Priority Data

Jan. 20, 1987 [JP] Japan .................. 62-10211

[51] Int. Cl.$^4$ .................. C09K 19/30; C09K 19; C09K 54; C07C 25/24; G02F 1/13
[52] U.S. Cl. .................. 252/299.63; 252/299.5; 570/128; 570/154; 350/350 R
[58] Field of Search .................. 252/299.5, 299.63; 570/128, 184; 250/350 R

[56] References Cited

U.S. PATENT DOCUMENTS

| | | | |
|---|---|---|---|
| 3,925,482 | 12/1975 | Jacques | 252/299.6 |
| 4,528,114 | 7/1985 | Petrzilka et al. | 252/299.63 |
| 4,670,182 | 6/1987 | Fujita et al. | 252/299.63 |
| 4,713,468 | 12/1987 | Takatsu et al. | 252/299.63 |
| 4,754,051 | 6/1988 | Sasaki et al. | 252/299.6 |

FOREIGN PATENT DOCUMENTS

| | | | |
|---|---|---|---|
| 60-155142 | 8/1985 | Japan | 252/299.63 |
| 61-197533 | 9/1986 | Japan | 252/299.6 |
| 61-260031 | 11/1986 | Japan | 252/299.6 |
| 61-26831 | 11/1986 | Japan | |
| 2155465 | 9/1985 | United Kingdom | |

Primary Examiner—Teddy S. Gron
Assistant Examiner—J. E. Thomas
Attorney, Agent, or Firm—Fred Philpitt

[57] ABSTRACT

A novel tolan type liquid crystal compound having a large optical anisotropy value, a high N-I transistion temperature and also a low viscosity, and a liquid crystal composition containing the same are provided, which compound is a 4-(trans-4''-alkylcyclohexyl-1''-ethyl)-3',4'-substituted- or 4-(trans-4''-alkylcyclohexyl-1'-ethyl)-4'-substituted-tolan expressed by the formula

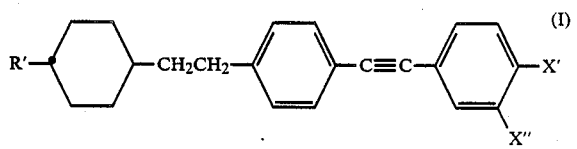

wherein R' represents an alkyl group of 1 to 10 carbon atoms, X' represents a halogen atom of F, Cl or Br and X'' represents hydrogen atom or a halogen atom of F, Cl or Br.

2 Claims, No Drawings

NOVEL TOLAN TYPE LIQUID CRYSTAL COMPOUND

BACKGROUND OF THE INVENTION

1. Field of the Invention

This invention relates to a tolan derivative as a novel compound and a liquid crystal composition containing the same.

2. Description of the Related Art

Display elements making use of liquid crystals utilize the optical anisotropy and dielectric anisotropy of liquid crystal substances, and include those . of various modes such as T-N (twisted nematic) type, DS (dynamic scattering) type, guest-host type, DAP type, etc. depending on their display modes. Properties required for liquid crystal substances used according to these modes each vary, but common properties thereto consist in that the substances exhibit liquid crystal phases in a temperature range as broad as possible and are stable to moisture, heat, air, etc. At present, however, there is no single compound which satisfies all of such requirements; hence it is the present status that liquid crystal compositions obtained by mixing several kinds of liquid crystal compounds or mixing similar compounds to liquid crystals with several kinds of liquid crystals have been used.

As examples of tolan derivatives used as a component of liquid crystal materials, compounds expressed by the following formulas are respectively disclosed in (1) Japanese patent application laid-open No. Sho 6055142/1985 and (2) Japanese patent application laidopen No. Sho 61-260031/1986:

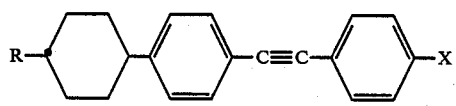

wherein R represents an alkyl group and X represents a halogen atom; and

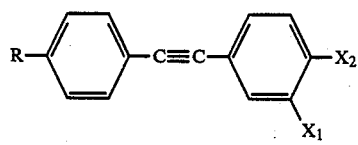

wherein R represents an alkyl group; $X_1$ represents hydrogen atom or a halogen atom; and $X_2$ represents a halogen atom.

These tolan compounds are liquid crystal materials characterized by having halogen atom(s) as a substituent and a large optical anisotropy value (hereinafter abbreviated to $\Delta n$).

Among these compounds, the compound (1) has a relativelyhigh clearing point, but since its compatibility with other liquid crystal compounds is inferior, crystals are deposited; hence the compound has a drawback that it is impossible to make use of its specific feature. The compound (2) has no liquid crystal phase and hence when it is used as a component of liquid crystal compositions, it has a drawback that it reduces N-I point of the compositions too much.

SUMMARY OF THE INVENTION

The object of the present invention is to provide a liquid crystal substance having a low viscosity and a superior compatibility with other liquid crystal compounds at low temperatures in addition to the above-mentioned specific features to thereby enhance the degree of freedom of choice of liquid crystal materials.

The present invention resides in
a 4-(trans-4''-alkylcyclohexyl-1''-ethyl)-3',-substituted-tolan or a 4-(trans-4''-alkylcyclohexyl-1''-ethyl)-4'-substituted-tolan expressed by the formula,

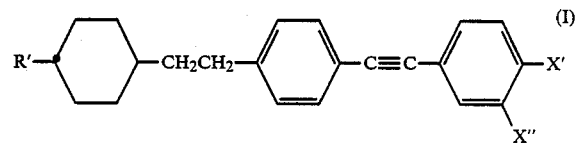

wherein R' represents an alkyl group of 1 to 10 carbon atoms, X' represents a halogen atom of F, Cl or Br and X'' represents hydrogen atom or a halogen atom of F, Cl or Br, and a liquid crystal composition containing the above-mentioned tolan derivative.

DETAILED DESCRIPTION OF PREFERRED EMBODIMENTS

The compound of the formula (I) of the present invention may be prepared for example according to the following preparation:

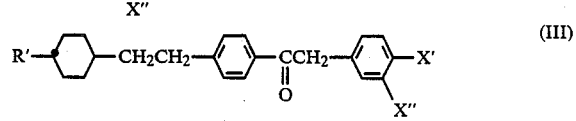

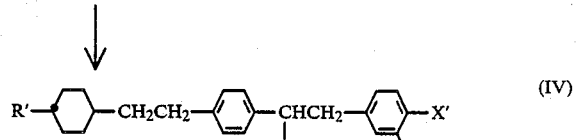

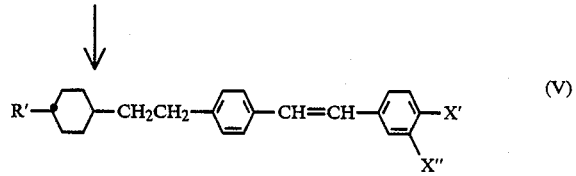

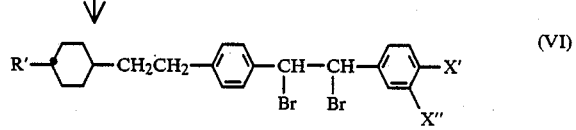

Firstly, a trans-4-alkylcyclohexylethylbenzene is reacted with a 4-substituted- or 3,4-substitutedphenylacetic acid chloride of the formula (II) and anhydrous aluminum chloride in carbon disulfide to obtain a ketone derivative of the formula (III), which is reacted with a reducing agent such as lithium aluminum hydride in a solvent such as anhydrous ether or anhydrous tetrahydrofuran to obtain a compound of the formula (IV).

Succesisvely, this alcohol derivative (IV) is subjected to dehydration reaction in the presence of a catalyst mentioned later in an inert organic solvent under the atmospheric pressure and at a reflux temperature to obtain an ethylene derivative of the formula (V). As the inert organic solvent, benzene, toluene, chloroform, carbon tetrachloride, methylene chloride, etc. are suitable, and as the catalyst Lewis acids such as aluminum chloride, tin tetrachloride, titanium tetrachloride, etc., mineral acids such as sulfuric acid, hydrochloric acid, phosphoric acid, etc., toluenesulfonic acid, etc. are usable.

Successively, bromine is attached to the compound (V) in a solvent such as methylene chloride, ethylene chloride, carbon tetrachloride, etc. to obtain a compound (VI), which is then reacted with potassium t-butoxide in a solvent such as ether or tetrahydrofuran, successively followed by a series of purification operations such as extraction, washing, recrystallization, etc. to obtain the objective compound of the formula (I).

The 4-(trans-4″-alkylcyclohexyl-1″-ethyl)-3′,′-substituted-tolan or 4-(trans-4″-alkylcyclohexyl-1″-ethyl)-4′-substituted-tolan of the present invention has the following specific features:

(i) its Δn value is large;
(ii) its viscosity is very low for the compound having a tricyclic structure; and
(iii) its clearing point is high and its nematic temperature range is broad.

Among the compounds of the present invention, those of the formula (I) wherein R′ represents ethyl, propyl, butyl or pentyl group and those of the formula (I) wherein X′ represents F and X″ represents hydrogen atom or X′ and X″ both represent F are preferred.

For example 4-(trans-4″-propylcyclohexyl-1″-ethyl)-4′-fluorotolan shown in an Example mentioned later is a stable liquid crystal compound having a Δn as large as about 0.23, a viscosity at 20° C. as small as 21 cp and a broad nematic temperature range, and also having various specific features well balanced.

Representative examples of preferred liquid crystal compounds used in admixture with the compound of the formula (I), as component(s) of the liquid crystal composition of the present invention, are 4-substituted-benzoic acid 4′-substituted-phenyl esters, 4-substituted-cyclohexanecarboxylic acid 4′-substituted-phenyl esters, 4-substituted-cyclohexanecarboxylic acid 4″-substituted-biphenylyl esters, 4-(4-substituted-cyclohexanecarbonyloxy)benzoic acid 4′-substituted-phenyl esters, 4-(4-substituted-cyclohexyl)benzoic acid 4′-substituted-phenyl esters, 4-(4-substituted-cyclohexyl)benzoic acid 4′-substituted-cyclohexyl esters, 4,4′-substituted-biphenyls, 4,4′-substituted-phenylcyclohexanes, 4,4″-substituted-terphenyls, 4,4″-substituted-biphenylylcyclohexanes, 2-(4′-substituted-phenyl)-5-substituted-pyrimidines, etc.

In order to prevent occurrence of interference fringes on the cell surface which cause damage to the cell appearance in liquid crystal display cells, it is necessary to set the product of the optical anisotropy (Δn) of a liquid crystal material filled in the cell and the cell thickness (d) μm to a specified value. In the case of practically used display cells, the value of Δn×d has been set to any one of 0.5, 1.0, 1.6 or 2.2. Since the value of Δn×d is set to a specified value as described above, it is possible to reduce the d value by using a liquid crystal material having a large Δn value. When the d value is reduced, the response time is reduced. Thus, a liquid crystal material having a large Δn value is important for forming a liquid crystal display cell having a high response rate and having no in&erference fringe. For reducing the response time, a low viscosity is also necessary. The compound of the formula (I) of the present invention is a novel nematic liquid crystal compound having a large Δn value, a high N-I transition temperature and further a low viscosity; hence when the compound of the formula (I) of the present invention is mixed with various mother liquid crystals, it is possible to prepare a practical liquid crystal material having a low viscosity, a large Δn value and a high N-I transition temperature.

The present invention will be described in more detail by way of Examples, but it should not be construed to be limited thereto.

The symbols C-S point, C-N point, S-N point and N-I point in Examples refer to crystalline-smectic phase transition point, crystalline-nematic phase transition point, smectic-nematic phase transition point and nematic-isotropic liquid phase transition point, respectively.

The cases where these symbols are enclosed by parentheses refer to monotropic point.

EXAMPLE 1

Preparation of 4-(trans-4″-propylcyclohexyl-1″-ethyl)-4′-fluorotolan

Anhydrous aluminum chloride (10.4 g, 0.078 mol) was added to carbon disulfide (100 ml), followed by adding 4-fluorophenylacetic acid chloride (11.2 g, 0.065 mol) under cooling, successively adding trans4-propylcyclohexylethylbenzene (15 g, 0.065 mol), then agitating the reaction mixture at room temperature for 10 hours, distilling off carbon disulfide, adding the residue to diluted HCl aqueous solution, agitating the mixture for one hour for decomposition, extracting deposited raw crystals with toluene (50 ml), water-washing, drying, distilling off toluene and recrystallizing residual solids from ethyl acetate to obtain the following compound (17.8 g):

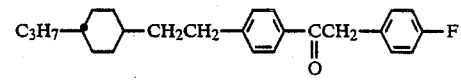

M.P.: 103.3° C.

This compound was dissolved in anhydrous tetrahydrofuran (50 ml), followed by dropwise adding the solution to a mixed solution of lithium aluminum hydride (1.0 g) with anhydrous tetrahydrofuran (50 m0, agitating the mixture at 0° C. for 2 hours, adding 20% by weight sulfuric acid (50 ml) to the reaction material to dissolve inorganic materials therein, extracting the resulting separated oily material with toluene (100 ml), washing the separated toluene solution with 10% aqueous solution of NaHCO₃, washing with water till washing water became neutral, drying the toluene solution over anhydrous sodium sulfate, adding p-toluenesulfonic acid (1.0 g) removing water to the outside of the system by heating the mixture under reflux, allowing the resulting material to cool down to room temperature after completion of the reaction, wasing the toluene solution with water till washing water became neutral, drying the resulting toluene solution over anhydrous sodium sulfate and recrystallizing from ethyl acetate to obtain the following compound (13.1 g):

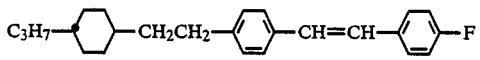

This compound exhibited the following liquid crystal phases: C-N point, 130.8° C. and N-I point, 186.3° C.

This compound was dissolved in methylene chloride (150 ml), followed by dropwise adding bromine (6.0 g, 0.037 mol) to the solution at room temperature, reacting the mixture for one hour, distilling off methylene chloride and recrystallizing the residual solids from benzene to obtain the following compound (10.9 g):

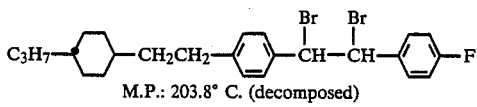

M.P.: 203.8° C. (decomposed)

This compound was then dissolved in anhydrous tetrahydrofuran (200 ml), followed by adding potassium t-butoxide (7.2 g, 0.064 mol) to the solution, agitating the mixture at 40° C. for 2 hours, adding water (400 ml) to the reaction mixture, extracting the resulting separated organic layer with toluene (100 ml), washing with water, drying, distilling off toluene and recrystallizing the residual solids from ethyl acetate to obtain the following objective compound (6.9 g):

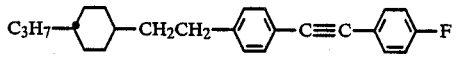

This product exhibited the following liquid crystal phases:
C-N point: 85.8° C.
(S-N point): 63.6° C.
N-I point) 148.8° C.

EXAMPLES 2-6

The following compounds were obtained in the same manner as in Example 1:
4-(trans-4''-butylcyclohexyl-1''-ethyl)-4'-fluorotolan
  C-S point: 75.1° C.
  S-N point: 78.0° C.
  N-I point: 145.8° C.
4-(trans-4'-pentylcyclohexyl-1''-ethyl)-4'-fluorotolan
  C-N point: 78.7° C.
  (S-N point): 75.6° C.
  N-I point: 149.8° C.
4-(trans-4''-propylcyclohexyl-1''-ethyl)-4'-chlorotolan
  C-N point: 103.1° C.
  N-I point: 177.4° C.
4-(trans-4''-ethylcyclohexyl-1''-ethyl)-3',4'-difluorotolan
  C-N point: 85.3° C.
  N-I point: 122.0° C.
4-(trans-4''-pentylcyclohexyl-1''-ethyl)-3',4'-difluorotolan
  C-N point: 85.4° C.
  N-I point: 125.3° C.

EXAMPLE 7

A liquid crystal composition A consisting of

| A | trans-4-propyl-(4-cyanophenyl)cyclohexane 30% by weight<br>trans-4-pentyl-(4-cyanophenyl)cyclohexane 40% by weight<br>trans-4-heptyl-(4-cyanophenyl)cyclohexane 30% by weight |
|---|---| has a N-I point of 52.1° C., a viscosity at 20° C. of 22.4 cp and an optical anisotropy Δn of 0.119. To this liquid crystal composition (85 parts by weight) was added 4-(trans-4''-propylcyclohexyl-1''-ethyl)-4'-fluorotolan (15 parts by weight) as a compound of the present invention shown in Example 1. The resulting liquid crystal composition had a N-I point raised up to 64.1° C., a viscosity at 20° C. reduced down to 22.0 cp and an optical anisotropy value raised up to 0.140. As seen from this Example, the compound of the formula (I) has an effectiveness of raising the N-I point of a mother liquid crystal composition up to a practically sufficient value without increasing its viscosity and also raising its Δn.

EXAMPLE 8

To the liquid crystal composition A (85 parts by weight) used in Example 7 was added 4-(trans-4''-pentylcyclohexyl-1''-ethyl)-4'-fluorotolan (15 parts by weight) shown in Example 3. The resulting liquid crystal composition had a N-I point of 64.6° C., a viscosity at 20° C. of 22.4 cp and a Δn of 0.135.

EXAMPLE 9

To the liquid crystal composition A (90 parts by weight) used in Example 7 was added 4-(trans-4''-propylcyclohexyl-1''-ethyl)-4'-chlorotolan (10 parts by weight) shown in Exmaple 4. The resulting liquid crystal composition had a N-I point of 62.6° C., a viscosity at 20° C. of 22.8 cp and a Δn of 0.134.

EXAMPLE 10

To the liquid crystal composition A (85 parts by weight) used in Example 7 was added 4-(trans-4''-ethylcyclohexyl-1''-ethyl)-3',4'-difluorotolan (15 parts by weight) shown in Example 5. The resulting liquid crystal composition had a N-I point of 59.3° C., a viscosity at 20° C. of 22.9 cp and a Δn of 0.132.

In addition, even when the liquid crystal compositions prepared in Examples 7 to 10 were allowed to stand at −30° C. for 20 days, no crystal was deposited.

What we claim is:

1. A 4-(trans-4''-alkylcyclohexyl-1''-ethyl)-3',4'-substituted-tolan or a 4-(trans-4''-alkylcyclohexyl1''-ethyl)-4'-substituted-tolan expressed by the formula

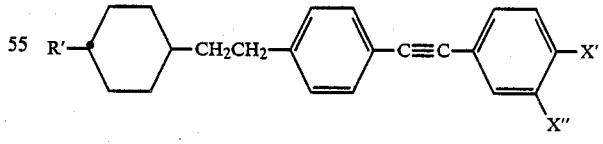

wherein R' represents an alkyl group of 1 to 10 carbon atoms, X' represents a halogen atom of F, Cl or Br and X'' represents hydrogen atom or a halogen atom of F, Cl or Br.

2. A liquid crystal composition comprising at least two components at least one of which is a 4-(trans-4''-alkylcyclohexyl-1''-ethyl)-3',4'-substituted-tolan or a 4-(trans-4''-alkylcyclohexyl-1''-ethyl)-4'-substituted-tolan as set forth in claim 1.

* * * * *